United States Patent
Michlig Gonzalez et al.

(10) Patent No.: US 10,092,028 B2
(45) Date of Patent: *Oct. 9, 2018

(54) COMPOSITIONS COMPRISING CINNAMALDEHYDE AND ZINC AND METHODS OF USING SUCH COMPOSITIONS

(71) Applicant: NESTEC S.A., Vevey (CH)

(72) Inventors: Stephanie Michlig Gonzalez, Le Mont-sur-Lausanne (CH); Jenny Meylan Merlini, Lausanne (CH); Susana Camacho, Lausanne (CH); Johannes Le Coutre, Pully (CH)

(73) Assignee: Nestec S.A., Vevey (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/327,108

(22) PCT Filed: Jun. 8, 2015

(86) PCT No.: PCT/EP2015/062696
§ 371 (c)(1),
(2) Date: Jan. 18, 2017

(87) PCT Pub. No.: WO2016/008642
PCT Pub. Date: Jan. 21, 2016

(65) Prior Publication Data
US 2017/0164648 A1    Jun. 15, 2017

Related U.S. Application Data

(60) Provisional application No. 62/026,157, filed on Jul. 18, 2014.

(51) Int. Cl.
| A23L 33/11 | (2016.01) |
| A23L 33/105 | (2016.01) |
| A23L 33/00 | (2016.01) |
| A23L 33/16 | (2016.01) |
| A61K 33/30 | (2006.01) |
| A61K 31/11 | (2006.01) |

(52) U.S. Cl.
CPC ........... *A23L 33/11* (2016.08); *A23L 33/105* (2016.08); *A23L 33/16* (2016.08); *A23L 33/30* (2016.08); *A61K 31/11* (2013.01); *A61K 33/30* (2013.01)

(58) Field of Classification Search
CPC ..................................................... A23L 33/11
USPC ......................................................... 514/701
See application file for complete search history.

(56) References Cited

U.S. PATENT DOCUMENTS 4,469,674 A * 9/1984 Shah ............... A61K 8/21
424/48

FOREIGN PATENT DOCUMENTS

| EP | 1654937 | 5/2006 |
| KR | 20120122597 | 11/2012 |
| WO | WO 200128503 | * 4/2001 ............. A61K 7/00 |

OTHER PUBLICATIONS

Joe Leech, MS on Jun. 4, 2017 (https://www.healthline.com/nutrition/10-proven-benefits-of-cinnamon).*
Poliquin Group, Supplements Articles:Top Ten Benefits of Zinc, Feb. 9, 2012.*
Kirkham et al. Diabetes Obes Metab. Dec. 2009;11(12):1100-13.*
Peterson, Journal of Alzheimer's Disease, vol. 17, No. 3, pp. 585-597, 2009.*
O'Halloran, The Journal of Clinical Investigation, vol. 123 No. 10 Oct. 2013.*
De Moura, Biol Trace Elem Res. Oct. 2013;155 (1):23-8.*
Bora, Chandramita "Wondrous and Proven Effects of Cinnamon on Weight Loss" printed from the Internet at http://www.buzzle.com/articles/cinnamon-weight-loss-effects.html, Nov. 21, 2012, 5 pages, XP055186730
Martino, Joe "Honey & Cinnamon—The Natural Cures & Health Benefits" printed from the Internet at http://www.collective-evolution.com/2014/02/23/honey-cinnamon-natural-curres-health-benefits/, Feb. 23, 2014, 11 pages, XP055186627.
Article entitled "Top Ten Benefits of Zinc—Poliquin Article" The Poliquin Group, printed from the Internet at http://main.poliquingroup.com/articlesmultimedia/articles/article/812/top_ten_benefits_of zinc.aspx, Sep. 2, 2012, 4 pages, XP055235866.
Article entitled "Health Benefits of Cinnamon", printed from the Internet at http://herbalismroots.com/health-benefits-of-cinnamon/, May 16, 2014, 3 pages, XP055235863.
Mintel "Water-Based Cinnamon Extract Capsules", printed from the Internet at http://www.gnpd.com/sinatra/recordpage/1127819/from_search/SUq4rtbplg/, Aug. 1, 2009, 3 pages, XP055235438.
Mintel "Instant Cocoa Drink Powder", printed from the Internet at http://www.gnpd.com/sinatra/recordpage/2375159/from_search/T516eG3Rde/, Apr. 1, 2014, 3 pages, XP055235458.
Chung et al. "A 5' adenosine monophosphate—activated protein kinase (AMPK) activator comprises cinnamic aldehyde as an active ingredient", Abstract of KR20100042410, vol. 2012, No. 63, Nov. 14, 2011, 2 pages, XP002734719.

* cited by examiner

*Primary Examiner* — Nizal S Chandrakumar
(74) *Attorney, Agent, or Firm* — K&L Gates LLP

(57) ABSTRACT

Compositions comprise an amount of cinnamaldehyde that is orally tolerable, thus avoiding an unpleasant mouth feeling, and also tolerable in the gastrointestinal tract. The amount of cinnamaldehyde is supplemented by zinc, and the combination is effective to increase at least one of energy expenditure, sympathetic nervous system activity, or fat oxidation, relative to a composition lacking cinnamaldehyde and zinc but otherwise identical. The composition comprising the combination of cinnamaldehyde and zinc can be used in a method to support weight managementor promote weight loss, a method for preventing obesity or overweight, and a method for treating obesity or overweight. In an embodiment, the composition comprising cinnamaldehydeis administered to a human. The composition comprising cinnamaldehyde may be a medicament, a food product or a supplement. The composition can improve one or more of insulin sensitivity, glucose tolerance, cognitive performance, cognition, mood or memory.

8 Claims, 8 Drawing Sheets

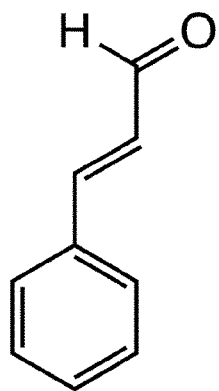
Fig. 1. The chemical structure of cinnamaldehyde.
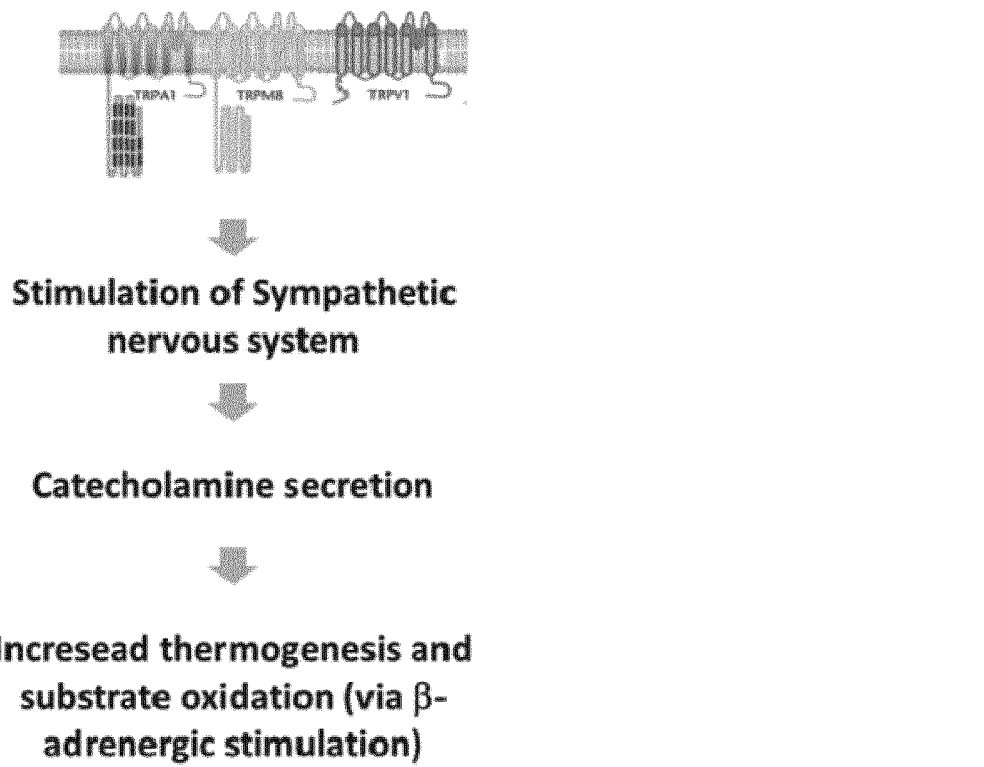
Fig. 2. Proposed mechanism of increased energy expenditure from cinnamaldehyde and zinc.

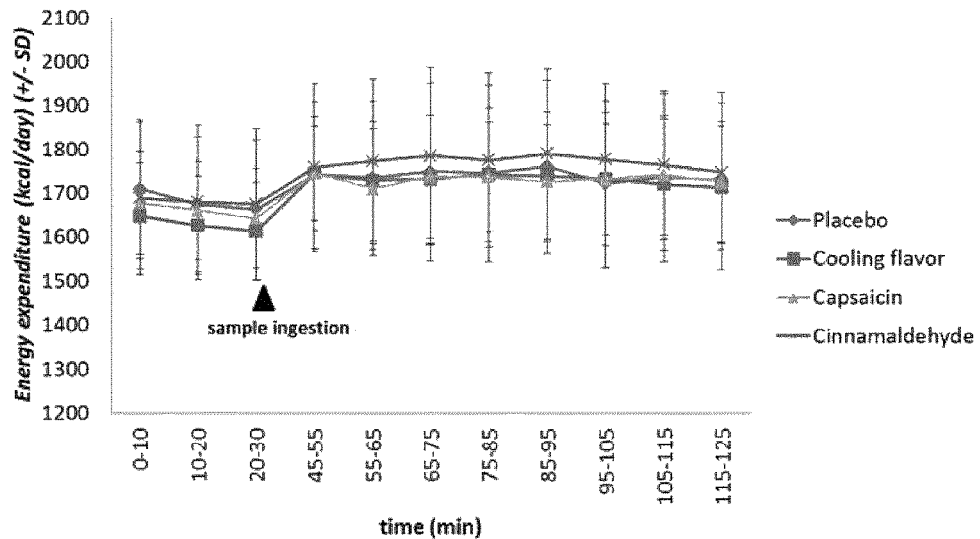
Fig. 3: Change in energy expenditure after ingestion of various compounds.
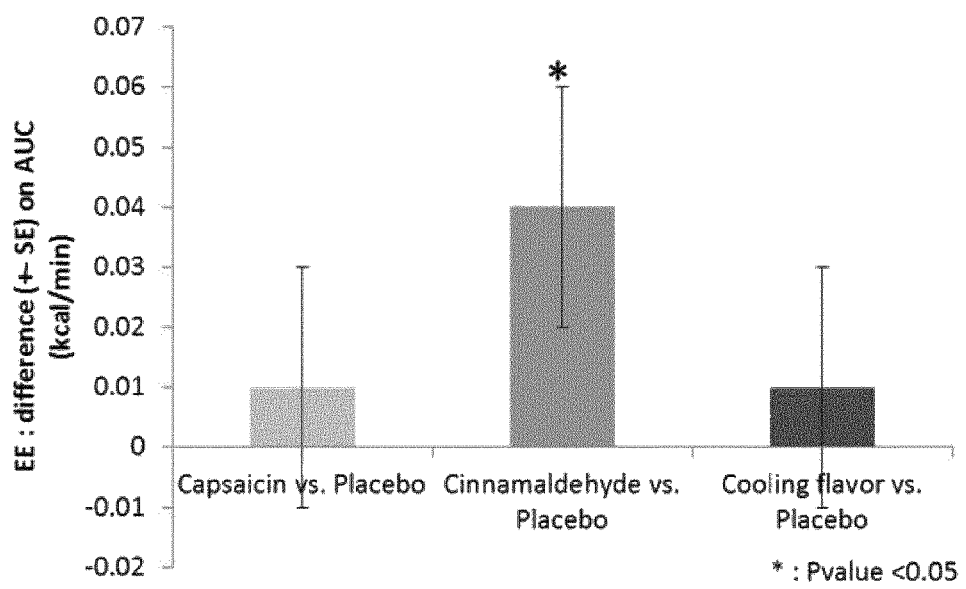
Fig. 4: Change in energy expenditure (AUC) after ingestion of various compounds.

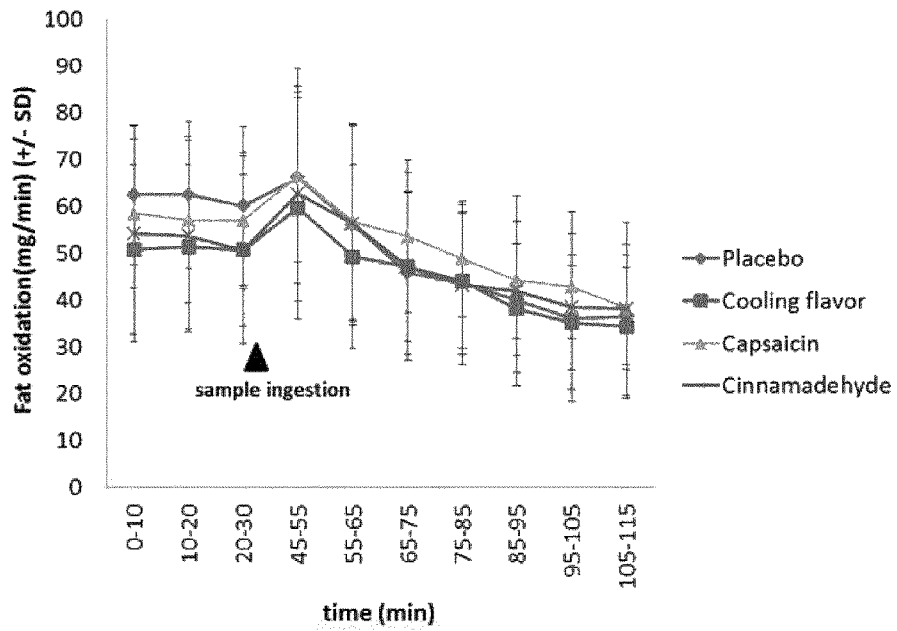
Fig. 5. Postprandial fat oxidation after ingestion of various compounds.
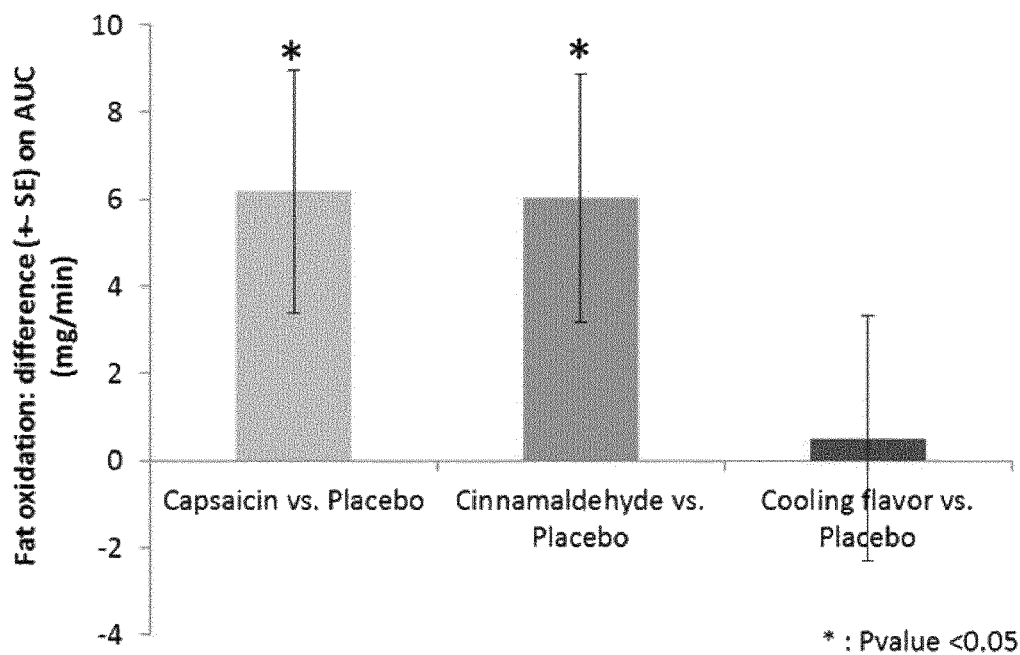
Fig. 6: Postprandial fat oxidation (AUC) after ingestion of various compounds.

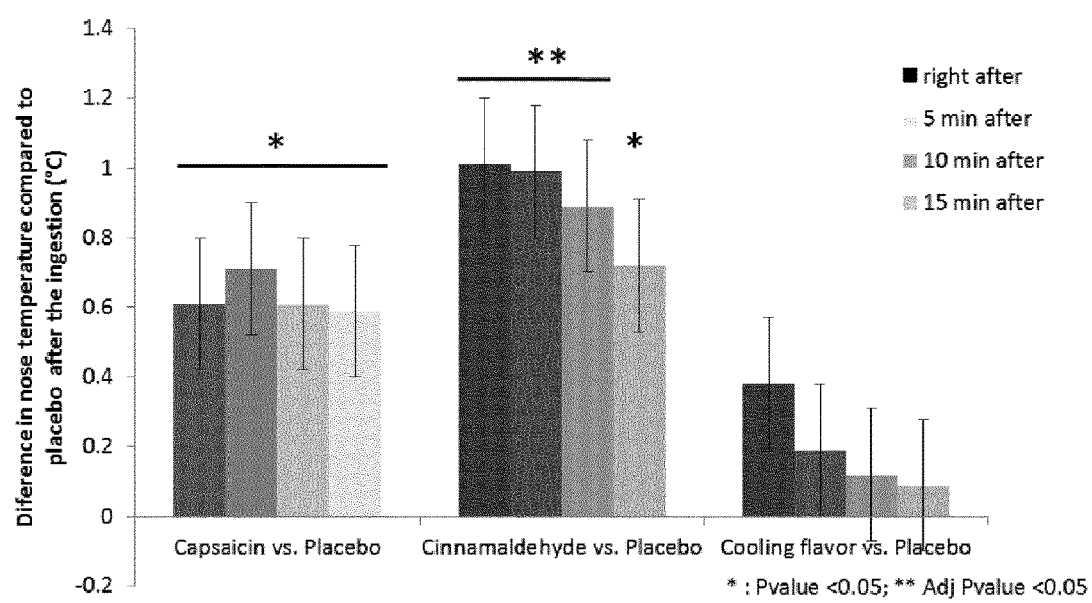
Fig. 7. Nose temperature after ingestion of various compounds.

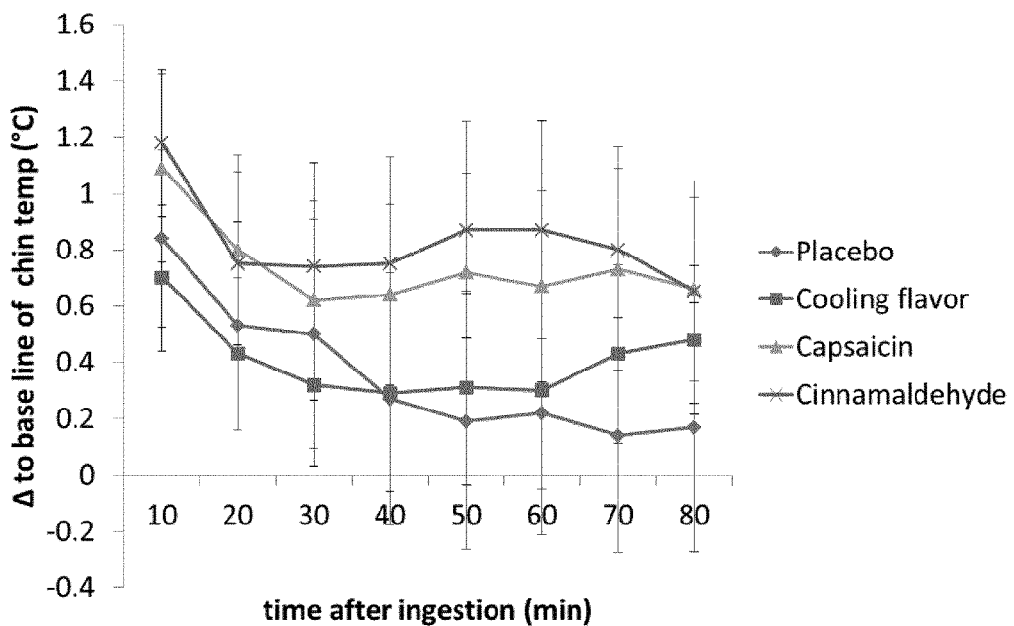
| Comparisons | Difference | SE | 98.33%CI | Raw p-value | Adjusted p-value |
| --- | --- | --- | --- | --- | --- |
| Z10 Cap vs Pl | 25.26 | 13.943 | [-9.583;60.104] | 0.0775 | 0.2325 |
| Z10 Cin vs Pl | 34.072 | 13.567 | [0.166;67.977] | 0.0162 | 0.0486 |
| Z10 CF vs Pl | 3.486 | 13.557 | [-30.394;37.367] | 0.7984 | 1 |
Fig. 8. Chin temperature after ingestion of various compounds, indicative of blood flow.

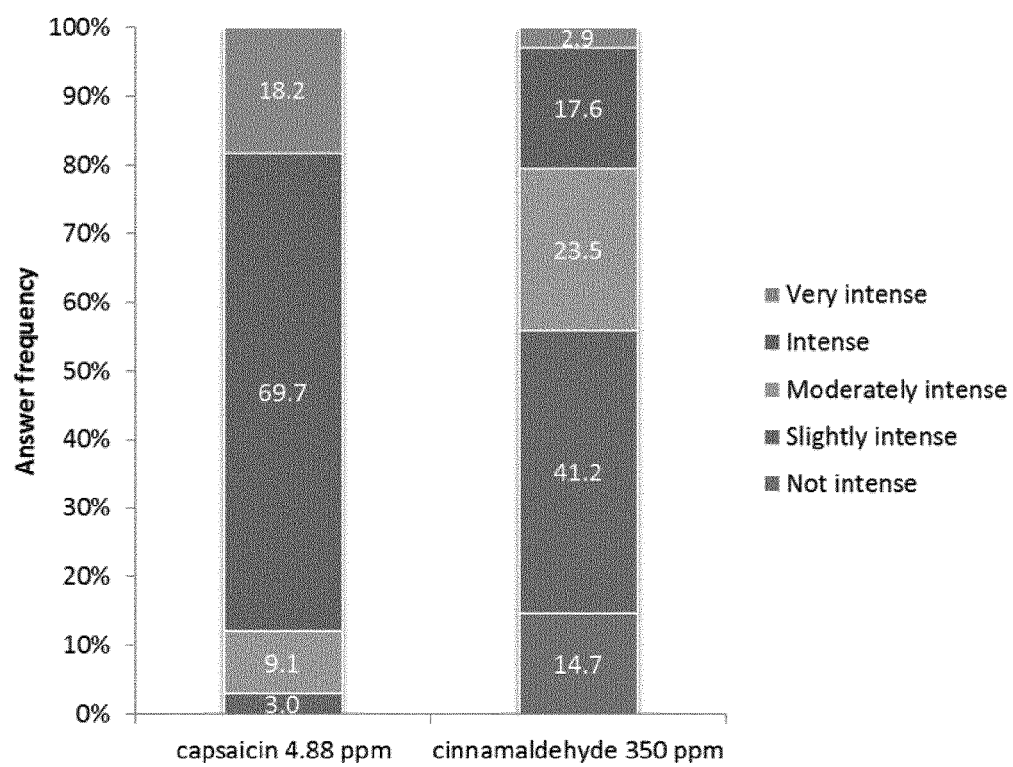
Fig. 9. Flavor intensity results from taste testing, comparing capsaicin and cinnamaldehyde.

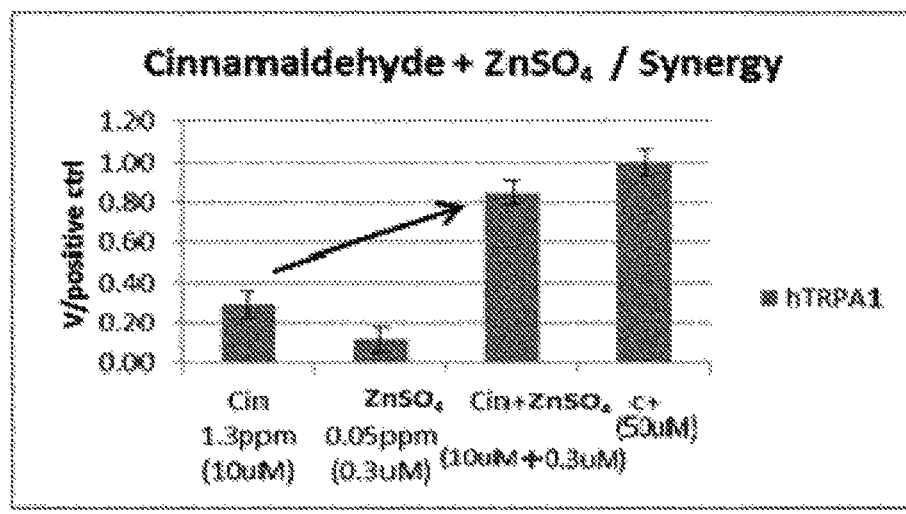
Fig. 10. *In vitro* evaluation of cinnamaldehyde and zinc synergy.

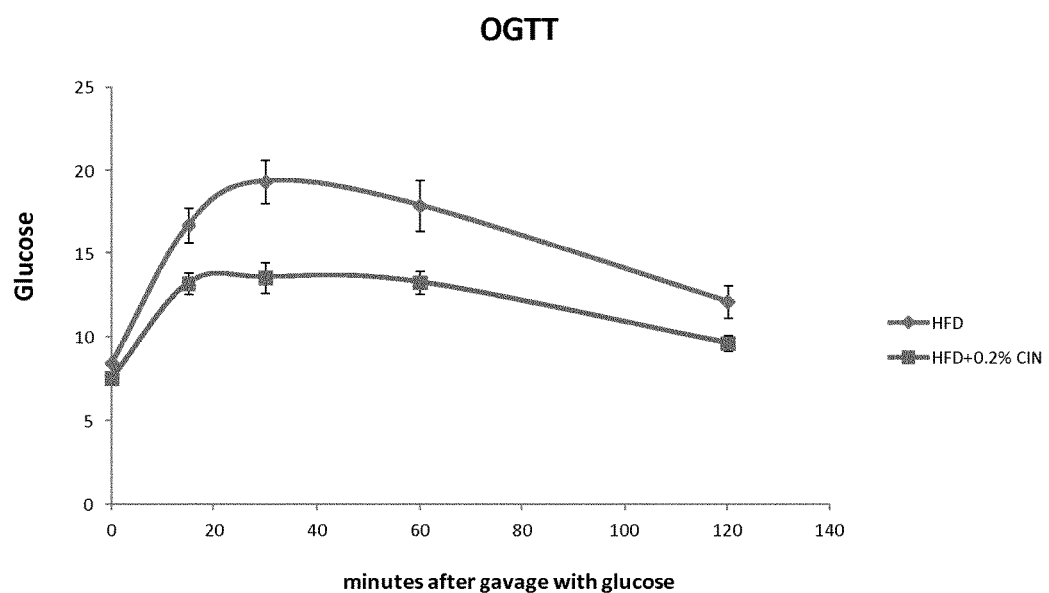
Fig. 11. Effect in mice of chronic ingestion of TRPA1 agonist cinnamaldehyde on insulin sensitivity.

COMPOSITIONS COMPRISING CINNAMALDEHYDE AND ZINC AND METHODS OF USING SUCH COMPOSITIONS

CROSS REFERENCE TO RELATED APPLICATIONS

The present application is a National Stage of International Application No. PCT/EP2015/062696, filed on Jun. 8, 2015, which claims priority to U.S. Provisional Patent Application Ser. No. 62/026,157, filed Jul. 18, 2014, the entire contents of which are being incorporated herein by reference.

BACKGROUND

The present disclosure generally relates to methods and compositions comprising cinnamaldehyde and zinc. More specifically, the present disclosure relates to administering an amount of cinnamaldehyde that is suitable for oral consumption and, in combination with zinc, increases energy expenditure and fat oxidation and/or improves one or more of insulin sensitivity, glucose tolerance, mood, memory or cognition.

During the past decades, the prevalence of obesity has increased worldwide to epidemic proportion. Approximately 1 billion of people worldwide are overweight or obese, conditions that increase mortality, mobility and economical costs. Obesity develops when energy intake is greater than energy expenditure, the excess energy being stored mainly as fat in adipose tissue. Body weight loss and prevention of weight gain can be achieved by reducing energy intake or bioavailability, increasing energy expenditure, and/or reducing storage as fat.

Research on the molecular mechanisms underlying pungent sensations revealed the existence of two cation channels, TRPV1 (transient receptor potential V1) and TRPA1 (transient receptor potential A1) that are expressed in the somatosensory fibers innervating the oral cavity. TRPV1 is the receptor for heat and burning sensations such as capsaicin, the spicy compound of chili peppers. TRPA1 responds to cold and pungent compounds; at moderate concentrations, TRPA1 agonists exhibit a pleasant tingling sensation.

The TRPV1 agonist capsaicin is well known as increasing energy expenditure and fat oxidation, but the efficient doses are intermediate to high (20 mg and more). See, e.g., Ludy et al, "The effects of hedonically acceptable red pepper doses on thermogenesis and appetite," Physiol. Behav., Mar. 1, 102(3-4): 251-8 (2011). Moreover, capsaicin is a particularly pungent and toxic compound. Physiological effects associated with oral administration of capsaicin include a burning sensation of heat from the mid-tongue to the throat, shortness of breath, fainting, nausea, and spontaneous vomiting. As a result, only small quantities of capsaicin may be administered without causing discomfort to the individual. Food products containing capsaicin are frequently not accepted by the consumer because such products provide a very unpleasant mouth feeling. In particular, the burning effects are considered to be very unsavory, affecting the consumption of the food product.

So far, the only spice-derived ingredient showing an impact on human metabolism is capsaicin. For example, a study that investigated the effect of mustard, horseradish, black pepper and ginger on energy balance and food intake in humans did not identify any effect of these raw spices. Gregersen et al., "Acute effects of mustard, horseradish, black pepper and ginger on energy expenditure, appetite, ad libitum energy intake and energy balance in human subjects," Br. J. Nutr., 5:1-8 (July 2012). However, the effective dosage of capsaicin is too intense to be included in a food product, due to spicy taste, or to be ingested, due to gastrointestinal intolerance.

The cinnamon-derived compound cinnamaldehyde is α,β-unsaturated aldehyde that activates TRPA1, but not TRPV1 or TRPM8, with an EC50 of approximately 10 μM. Cinnamaldehyde interacts with TRPA1 in a covalent manner. Cinnamaldehyde has a flavor that is less intense than capsaicin. Nevertheless, cinnamaldehyde is pungent at relatively high concentrations and has a strong cinnamon flavor.

Another condition adversely affecting some individuals is that their body tissues do not respond properly to insulin. Insulin receptors in the tissues cease to function adequately, and gluco-dependent cells fail to recognize the presence of insulin. As a result, the pancreas needs to secrete more insulin to help glucose enter these cells. The pancreas tries to keep up with this increased demand for insulin by producing more. This phenomenon is called insulin resistance (also known as low insulin sensitivity). Many people with insulin resistance have high levels of both glucose and insulin circulating in their blood at the same time. Eventually, the pancreas fails to keep up with the body's need for insulin, leading to Type II diabetes.

Insulin resistance and Type II diabetes are associated with increased risk of heart attacks, strokes, amputation, diabetic retinopathy, and kidney failure. For extreme cases, circulation of limbs is affected, potentially requiring amputation. Loss of hearing, eyesight, and cognitive ability has also been linked to these conditions Management of insulin resistance in children and adults is essentially based on dietary and lifestyle changes, including healthier dietary habits and increased exercise. These practices can be very efficient in improving insulin sensitivity and in slowing the progression of the disease, but they are difficult to apply and actually not followed by most patients. Type II diabetes can be treated with drugs promoting insulin sensitivity, but their efficacy in reducing the rate of progression of the disease is quite low. Insulin treatment is required during the most advanced phases of the disease.

Products containing n-3 polyunsaturated fatty acids, fibers, oligosaccharides and even probiotics have been proposed as nutritional solutions to improve insulin sensitivity and to reduce insulin resistance. However, the efficacy of these nutritional interventions is quite marginal and even controversial, with studies showing no or even deleterious effects.

The TRPV1 agonist capsaicin can improve insulin sensitivity; however, as noted above, capsaicin is a particularly pungent and toxic compound, and the effective dosage of capsaicin is too intense to be included in a food product, due to spicy taste, or to be ingested, due to gastrointestinal intolerance.

Yet another condition adversely affecting some individuals is impaired neurotransmission, for example low levels of neurotransmitters such as epinephrine. Impaired neurotransmission is connected to mood disorders such as depression, anxiety disorders, and increased susceptibility to stress, and also connected to cognitive dysfunction.

Carbohydrate-rich foods are known for providing important metabolic fuel for physical performance, but their effects on mood and cognitive performance are not very clear. However, irritability and aggression are influenced by individual differences in insulin release, the frequency that meals are eaten, and the effect of these meals on blood glucose values. Benton, "Carbohydrate ingestion, blood glucose and mood," Neuroscience and Biobehavioral Reviews, 26:293-308 (2002). Furthermore, the ability to control the levels of blood glucose is related to both mood and cognition. For example, in a study in which participants were given an oral glucose tolerance test and cognitive tests, the older age group showed that those with poorer glucose tolerance forgot more words and had slower decision times; and, in those participants with poor glucose tolerance, a tendency for blood glucose to fall below baseline values was associated with better mood and faster working memory. Young and Benton, "The nature of the control of blood glucose in those with poorer glucose tolerance influences mood and cognition," Metab. Brain Dis. (Mar. 26, 2014).

SUMMARY

The present inventors surprisingly and unexpectedly identified a synergy of cinnamaldehyde and zinc on the pharmacological activity of TRPA1. Using this synergy, the effective amount of cinnamaldehyde can be decreased by supplementing the cinnamaldehyde with small amount of zinc. The decreased amount of cinnamaldehyde can reduce the aromatic impact while maintaining a good efficacy on the activity of TRPA1. Moreover, the synergy only requires a low concentration of zinc (<1 µM), which is advantageous because individuals may already receive zinc through their diet, especially if supplements are consumed.

The present inventors identified a synergy of cinnamaldehyde and zinc on the pharmacological activity of TRPA1 expressed in a cellular model. To the best knowledge of the inventors, this is the first time that the synergy of this combination has been shown. This synergy is significant because cinnamaldehyde obtains a significantly higher impact on energy expenditure and sympathetic nervous system activity and an equivalent effect on fat oxidation compared to capsaicin, at a flavoring level of cinnamaldehyde judged significantly less intense than capsaicin.

Moreover, without wishing to be bound by theory, the present inventors believe that synergistic activation of TRPA1 by the combination of cinnamaldehyde and zinc is effective to improve one or more of insulin sensitivity, glucose tolerance, mood, memory or cognition. Accordingly, in a general embodiment, the present disclosure provides a method for weight maintenance. The method comprises administering to an individual in need thereof a composition comprising cinnamaldehyde and zinc.

In an embodiment, the cinnamaldehyde is present in the composition in an amount that is safe and tolerable to ingest and, in combination with the zinc, effective to increase at least one characteristic selected from the group consisting of energy expenditure, sympathetic nervous system activity, and fat oxidation.

In an embodiment, the composition comprises cinnamon essential oil extract that provides at least a portion of the cinnamaldehyde.

In an embodiment, at least a portion of the cinnamaldehyde is selected from the group consisting of isolated cinnamaldehyde and synthesized cinnamaldehyde.

In another embodiment, the present disclosure provides a method for promoting weight loss. The method comprises administering to an individual in need thereof a composition comprising cinnamaldehyde and zinc.

In another embodiment, the present disclosure provides a method for preventing obesity or overweight. The method comprises administering to an individual at risk thereof a composition comprising cinnamaldehyde and zinc.

In another embodiment, the present disclosure provides a method for treating obesity. The method comprises administering to an obese individual a composition comprising a therapeutically effective amount of cinnamaldehyde and zinc.

In another embodiment, the present disclosure provides a composition for weight loss comprising cinnamaldehyde and zinc.

In an embodiment, the cinnamaldehyde is present in the composition in an amount that is safe and tolerable to ingest and, in combination with the zinc, effective to increase at least one characteristic selected from the group consisting of energy expenditure, sympathetic nervous system activity, and fat oxidation.

In an embodiment, the composition is a food product in which the cinnamaldehyde is present at flavouring concentration from 31.87 ppm (condiments, relishes) up to 6191 ppm (chewing gum) (Fenaroli's Handbook; Burdock, 2010).

In an embodiment, the composition is a food product in which the cinnamaldehyde:zinc ratio is 1:0.5 to 1:0.005, preferably 1:0.03 (in molarity).

In an embodiment, the composition further comprises an additional ingredient in a therapeutically effective amount to promote weight maintenance or weight loss.

In another embodiment, the present disclosure provides a method for promoting weight loss. The method comprises administering a composition comprising cinnamaldehyde and zinc to an individual on a weight loss program.

In an embodiment, the weight loss program is selected from the group consisting of a low-fat diet, a low-carbohydrate diet, a low-calorie diet, a very low-calorie diet, endurance training, strength training, and combinations thereof.

In another embodiment, the present disclosure provides a method for making a food product for weight loss. The method comprises adding cinnamaldehyde and zinc to a component selected from the group consisting of protein, carbohydrate, fat and combinations thereof.

In another embodiment, the present disclosure provides a method for improving a characteristic selected from the group consisting of insulin resistance, glucose tolerance and a combination thereof. The method comprises administering to an individual in need thereof a composition comprising cinnamaldehyde and zinc.

In an embodiment, the individual is selected from the group consisting of an infant born preterm, an infant experiencing intrauterine growth restriction, a pregnant woman suffering from gestational diabetes, a human suffering from insulin resistance, a human suffering from impaired glucose tolerance, and a human suffering from type II diabetes.

In an embodiment, the cinnamaldehyde is present in the composition in an amount that is safe and tolerable to ingest and, in combination with the zinc, effective to improve the characteristic selected from the group consisting of insulin resistance, glucose tolerance and a combination thereof.

In an embodiment, the composition is a food product in which the cinnamaldehyde is present at a flavouring concentration from 31.87 ppm to 6191 ppm.

In an embodiment, the composition comprises cinnamon essential oil extract that provides at least a portion of the cinnamaldehyde.

In an embodiment, at least a portion of the cinnamaldehyde is selected from the group consisting of isolated cinnamaldehyde and synthesized cinnamaldehyde.

In an embodiment, the composition is administered to the individual at least once a day for at least one week.

In another embodiment, the present disclosure provides a composition comprising cinnamaldehyde and zinc. The cinnamaldehyde is present in the composition in an amount that is safe and tolerable to ingest and, in combination with the zinc, effective to improve at least one characteristic selected from the group consisting of insulin sensitivity and glucose tolerance.

In an embodiment, the composition is a food product in which the cinnamaldehyde is present at a flavouring concentration from 31.87 ppm to 6191 ppm.

In an embodiment, the composition is a food product in which the cinnamaldehyde:zinc ratio is 1:0.5 to 1:0.005.

In an embodiment, the composition is a food product comprising a component selected from the group consisting of protein, carbohydrate, fat and combinations thereof.

In another embodiment, the present disclosure provides a method for improving one or more of cognitive performance, cognition, mood, or memory comprising administering to an individual in need thereof a composition comprising cinnamaldehyde and zinc.

In an embodiment, the individual has a condition selected from the group consisting of cognitive decline, mild cognitive impairment, dementia, a mood disorder, memory loss, and combinations thereof.

In an embodiment, the composition is administered to the individual at least once a day for at least one week.

In another embodiment, the present disclosure provides a method for making a food product, the method comprising adding cinnamaldehyde and zinc to a component selected from the group consisting of protein, carbohydrate, fat and combinations thereof, the cinnamaldehyde is present in the composition in an amount that is safe and tolerable to ingest and, in combination with the zinc, effective to improve at least one characteristic selected from the group consisting of insulin sensitivity, glucose tolerance, cognitive performance, cognition, mood, and memory in an individual that consumes the food product.

An advantage of the present disclosure is to increase energy expenditure.

Another advantage of the present disclosure is to increase sympathetic nervous system activity.

Still another advantage of the present disclosure is to increase fat oxidation.

Yet another advantage of the present disclosure is to increase energy expenditure, sympathetic nervous system activity, and fat oxidation with a compound that can be easily and safely used in food products.

An additional advantage of the present disclosure is to increase energy expenditure, sympathetic nervous system activity, and fat oxidation with a naturally-occurring compound that can be found in spices.

Another advantage of the present disclosure is to increase energy expenditure, sympathetic nervous system activity, and fat oxidation with tolerable side effects or no side effects.

Yet another advantage of the present disclosure is to support weight management, promote weight loss, and/or treat or prevent obesity or overweight.

Still another advantage of the present disclosure is to increase energy expenditure, sympathetic nervous system activity, and fat oxidation with a compound that has increased acceptability, reduced pungency, and improved tolerance in the gastrointestinal tract relative to capsaicin.

Another advantage of the present disclosure is to supplement cinnamaldehyde with zinc so that less cinnamaldehyde is required to increase energy expenditure.

Yet another advantage of the present disclosure is to improve insulin sensitivity and/or glucose tolerance.

Still another advantage of the present disclosure is to improve insulin sensitivity and/or glucose tolerance with a compound that can be easily and safely used in food products.

An additional advantage of the present disclosure is to improve insulin sensitivity and/or glucose tolerance with a naturally-occurring compound that can be found in spices.

Another advantage of the present disclosure is to improve insulin sensitivity and/or glucose tolerance with tolerable side effects or no side effects.

Yet another advantage of the present disclosure is to improve insulin sensitivity and/or glucose tolerance with a compound that has increased acceptability, reduced pungency, and improved tolerance in the gastrointestinal tract relative to capsaicin.

Still another advantage of the present disclosure is to improve at least one of mood, memory or cognition.

Still another advantage of the present disclosure is to improve at least one of mood, memory or cognition with a compound that can be easily and safely used in food products.

An additional advantage of the present disclosure is to improve at least one of mood, memory or cognition with a naturally-occurring compound that can be found in spices.

Another advantage of the present disclosure is to improve at least one of mood, memory or cognition with tolerable side effects or no side effects.

Yet another advantage of the present disclosure is to improve at least one of mood, memory or cognition with a compound that has increased acceptability, reduced pungency, and improved tolerance in the gastrointestinal tract relative to capsaicin.

Additional features and advantages are described herein, and will be apparent from, the following Detailed Description and the Figures.

BRIEF DESCRIPTION OF THE FIGURES

FIG. 1 shows the chemical structure of cinnamaldehyde.

FIG. 2 shows a proposed mechanism by which cinnamaldehyde can increase energy expenditure, sympathetic nervous system activity, and fat oxidation.

FIG. 3 shows a graph of energy expenditure as a function of time elapsed after ingestion of various compounds.

FIG. 4 shows a graph of energy expenditure based on AUC after ingestion of various compounds.

FIG. 5 shows a graph of postprandial fat oxidation as a function of time elapsed after ingestion of various compounds.

FIG. 6 shows a graph of postprandial fat oxidation based on AUC after ingestion of various compounds.

FIG. 7 shows a graph of nose temperature increases experienced after ingestion of various compounds.

FIG. 8 shows a graph and a table of chin temperature, relative to baseline, as a function of time elapsed after ingestion of various compounds.

FIG. 9 shows taste testing results comparing 4.88 ppm of capsaicin and 350 ppm of cinnamaldehyde.

FIG. 10 shows a graph of in vitro measurement of the activity of TRP channels expressed in CHO cells by measuring the intracellular calcium concentration with a fluorescent dye.

FIG. 11 shows a chart of insulin sensitivity in mice with chronic ingestion of cinnamaldehyde or control.

DETAILED DESCRIPTION

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number. Moreover, all numerical ranges herein should be understood to include all integers, whole or fractions, within the range. The compositions disclosed herein may lack any element that is not specifically disclosed herein. Thus, a disclosure of an embodiment using the term "comprising" includes a disclosure of embodiments "consisting essentially of" and "consisting of" the components identified.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

As used herein, an "effective amount" is an amount that prevents a deficiency, treats a disease or medical condition in an individual or, more generally, reduces symptoms, manages progression of the diseases or provides a nutritional, physiological, or medical benefit to the individual.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment.

"Overweight" is defined for a human as a BMI between 25 and 30. "Obese" is defined for a human as a BMI greater than 30. "Weight loss" is a reduction of the total body weight. Weight loss may, for example, refer to the loss of total body mass in an effort to improve fitness, health, and/or appearance. "Weight management" or "weight maintenance" relates to maintaining a total body weight. For example, weight management may relate to maintaining a BMI in the area of 18.5-25 which is considered to be normal.

As set forth above, the present inventors surprisingly and unexpectedly found a synergy of cinnamaldehyde and zinc on the pharmacological activity of TRPA1. Using this synergy, the effective amount of cinnamaldehyde can be decreased by supplementing the cinnamaldehyde with small amount of zinc. Consequently, unlike cinnamaldehyde in the absence of zinc, the combination of cinnamaldehyde and zinc can impact energy expenditure, sympathetic nervous system activity, and fat oxidation at concentrations in food that are safe and tolerable both in flavor/taste and in the gastrointestinal tract. Moreover, the synergy only requires a low concentration of zinc (in vitro <1 µM). Without being bound by theory, the inventors believe that cinnamaldehyde and zinc synergistically stimulate the sympathetic nervous system and, as a result, catecholamine secretion. The increased catecholamine secretion enhances thermogenesis and substrate oxidation by β-adrenergic stimulation. See FIG. 2.

Accordingly, the composition provided by the present disclosure comprises an amount of the cinnamaldehyde that is safe and orally tolerable, for example does not cause an unpleasant mouth feeling, and, in combination with the zinc, also effective to increase at least one of energy expenditure, sympathetic nervous system activity, or fat oxidation, relative to an otherwise identical composition lacking cinnamaldehyde and zinc. The composition can be administered to an individual at least once a day for at least one week, preferably for at least one month.

Cinnamaldehyde is available commercially. The cinnamaldehyde in the composition can be provided in a cinnamon essential oil extract, for example an extract from steam distillation of the oil of cinnamon bark; can be isolated cinnamaldehyde, for example isolated from cinnamon essential oil; or can be synthesized cinnamaldehyde, for example the product of aldol condensation of benzaldehyde and acetaldehyde. The concentration of cinnamaldehyde in the composition is preferably at flavouring concentration from 31.87 ppm (condiments, relishes) up to 6191 ppm (chewing gum) (Fenaroli's Handbook; Burdock, 2010). In an embodiment, the cinnamaldehyde is present in composition in an amount of about 100.0 ppm or less.

As non limiting examples, the cinnamaldehyde can be present in the following compositions as follows:
  alcoholic beverage: up to 498.8 ppm, such as about 435.6 ppm
  baked good: up to 367.4 ppm, such as about 273.8 ppm
  chewing gum: up to 6191.0 ppm, such as about 1533.0 ppm
  condiment or relish: up to 31.87 ppm, such as about 17.48 ppm
  frozen dairy product: up to 77.96 ppm, such as about 72.98 ppm
  fruit ice: up to 900.0 ppm, such as 900.0 ppm
  gelatin or pudding: up to 109.4 ppm, such as about 100.3 ppm
  gravy: up to 800.0 ppm, such as about 640.0 ppm
  hard candy: up to 1003.0 ppm, such as about 792.2 ppm
  meat product: up to 39.09 ppm, such as about 6.97 ppm
  non-alcoholic beverage: up to 67.82 ppm, such as about 52.71 ppm soft candy: up to 370.0 ppm, such as 370.0 ppm Preferred forms of zinc include zinc chloride, zinc sulfate, zinc lactate and zinc citrate. The cinnamaldehyde:zinc ratio is preferably 1:0.5 to 1:0.005, more preferably 1:0.03 (in molarity).

In an embodiment, the composition comprising cinnamaldehyde and zinc can be used in a method to support weight management or promote weight loss. For example, the composition can be administered to an individual, such as a mammal, that is managing their weight or undergoing a weight loss program. The weight loss program may include, for example, a weight loss diet (e.g., one or more of a low-fat diet, for example a diet with less than 20% of the calories from fat, preferably less than 15% from fat; a low-carbohydrate diet, for example a diet with less than 20% of the calories from carbohydrates; a low-calorie diet, for example a diet with less calories per day relative to the individual's previous intake before the diet, or a diet with less calories per day relative to an average person of similar body type; or a very low-calorie diet, for example a diet with 800 kcal (3,300 kJ) per day or less). Additionally or alternatively, the weight loss program may include a weight loss training regimen (e.g. endurance and/or strength training). In another embodiment, the composition comprising cinnamaldehyde and zinc can be used in a method for preventing obesity or overweight by administering the composition to an individual at risk thereof. In yet another embodiment, the composition comprising cinnamaldehyde and zinc can be used in a method for treating obesity or overweight by administering the composition to an individual in need thereof. In an embodiment, the composition comprising cinnamaldehyde and zinc is administered to a mammal, such as a human. The composition can also comprise an additional weight loss ingredient.

As shown in FIG. 11, mice chronically fed a high fat diet containing 0.2 wt % cinnamaldehyde had improved insulin sensitivity relative to mice fed the same high fat diet without cinnamaldehyde. Accordingly, the composition comprising an amount of the cinnamaldehyde that is safe and orally tolerable, for example does not cause an unpleasant mouth feeling, and, in combination with the zinc, also effective to increase sympathetic nervous system activity relative to an otherwise identical composition lacking cinnamaldehyde and zinc, can also improve insulin sensitivity and/or glucose tolerance. The composition can thereby reduce glycemia.

In an embodiment, the composition comprising cinnamaldehyde and zinc can be administered in a method for improving insulin sensitivity and/or glucose tolerance in an individual in need thereof. The composition can be administered to an infant (a child under the age of 12 months) born preterm and/or experiencing intrauterine growth restriction (IUGR), a pregnant woman suffering from gestational diabetes; or a child (up to twelve years of age), an adolescent (twelve to eighteen years of age), or an adult (over eighteen years of age) suffering from insulin resistance and/or type II diabetes, such as an animal such as a human. The composition can reduce glycemia by improving insulin sensitivity and/or glucose tolerance in the subject. The composition can be administered at least once a day for at least one week, preferably at least one month, and more preferably at least one year.

As noted above, there is a direct link between glucose tolerance and mood, memory and cognition. For example, in a study in which participants were given an oral glucose tolerance test and cognitive tests, the older age group showed that those with poorer glucose tolerance forgot more words and had slower decision times; and, in those participants with poor glucose tolerance, a tendency for blood glucose to fall below baseline values was associated with better mood and faster working memory. See, e.g., Young and Benton (2014). Therefore, without being bound by theory, the inventors believe that cinnamaldehyde and zinc synergistically enhance insulin sensitivity and/or glucose tolerance and can thereby improve one or more of mood, memory or cognition.

Accordingly, in an embodiment, the composition comprising cinnamaldehyde and zinc can be administered in a method of improving one or more of cognitive performance, cognition, mood or memory in an individual in need thereof. The composition can treat or prevent one or more of cognitive decline, mild cognitive impairment, dementia, a mood disorder, or memory loss in an individual having one or more of these conditions. The composition can be administered at least once a day for at least one week, preferably at least one month, and more preferably at least one year. The composition can be administered to an infant (a child under the age of twelve months), a child (up to twelve years of age), an adolescent (twelve to eighteen years of age), an adult (over eighteen years of age), or an elderly individual (past the first two thirds of the average expected lifespan in its country of origin, preferably past the first three quarters of the average expected lifespan in its country of origin; an elderly human is a person with a chronological age of 65 years or older).

Cognitive performance may be expressed as ability and speed of learning, ability and speed of solving intellectual problems, ability to form and recall memories, reaction time, and the like. Cognition is understood as mental processes such as comprehension, inference, decision-making, planning, learning, memory, association, concept formation, language, attention, perception, action, problem solving and mental images. Cognitive decline may manifest as reduced memory; forgetfulness; word or name-finding problems; and/or decline in memory, concentration, ability to plan or organize, ability to perform complex tasks, and/or cognitive performance; and may result from age, stress, disease, or other grounds. Cognitive impairment may manifest in one or more of short-term memory loss, diminished capacity to learn, diminished rate of learning, or diminished attention.

The term "mood" refers to a state or quality of feeling (an emotional state) at a particular time. Moods differ from simple emotions in that they are less specific, less intense, and less likely to be triggered by a particular stimulus or event. Moods generally have either a positive or negative valence. An improved mood may comprise one or more of a decreased anxiety level, a decreased stress level, an increased perceived energy level, or a more positive emotional state.

The composition comprising cinnamaldehyde and zinc may be a medicament, a food product, a medical food, an oral nutritional supplement, a nutritional composition, an oral cosmetics or a supplement to a food product and is preferably orally administered. A medical food product is specially formulated and intended for the dietary management of diseases or medical conditions (e.g., prevent or treat diseases or undesirable medical conditions). A medical food product can provide clinical nutrition, for example fulfilling special nutritional needs of patients with a medical condition or other persons with specific nutritional needs. A medical food product can be in the form of a complete meal, part of a meal, as a food additive, or a powder for dissolution.

A food product, medical food or nutritional composition includes any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

A food product, medical food or nutritional composition can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as a rice crackers), and dairy products.

A supplement may be in the form of tablets, capsules, pastilles or a liquid, for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The supplement can be added in a product acceptable to the consumer as an ingestible carrier or support. Non-limiting examples of such carriers or supports are a pharmaceutical, a food composition, and a pet food composition. Non-limiting examples for food and pet food compositions are milks, yogurts, curds, cheeses, fermented milks, milk-based fermented products, fermented cereal based products, milk-based powders, human milks, preterm formulas, infant formulas, oral supplements, and tube feedings.

EXAMPLES

The following non-limiting examples present scientific data developing and supporting the concept of administering the combination of cinnamaldehyde and zinc to synergistically activate TRPA1 to increase at least one of energy expenditure, sympathetic nervous system activity, or fat oxidation and/or to improve at least one of insulin sensitivity, glucose tolerance, cognitive performance, cognition, mood, or memory, without imparting an intolerable taste or gastrointestinal effect.

Example 1

Human subjects were administered placebo, a cooling flavor, capsaicin, or cinnamaldehyde. The energy expenditure was measured over the eighty minutes following ingestion. FIG. 3 shows a graph of energy expenditure as a function of time elapsed after ingestion of the various compounds. FIG. 4 shows a graph of energy expenditure based on AUC after ingestion of the various compounds. FIGS. 3 and 4 demonstrate that energy expenditure is increased after cinnamaldehyde ingestion compared to placebo.

The postprandial fat oxidation was measured over the 90 minutes following ingestion of the various compounds. FIG. 5 shows a graph of postprandial fat oxidation as a function of time elapsed after ingestion of the various compounds. FIG. 6 shows a graph of postprandial fat oxidation based on AUC after ingestion of various compounds. FIGS. 5 and 6 demonstrate that postprandial fat oxidation is maintained at higher levels after cinnamaldehyde ingestion compared to placebo.

The nose temperature of the subjects was analyzed over the fifteen minutes following ingestion of the various compounds. FIG. 7 shows a graph of the nose temperature increases that were experienced after ingestion of the various compounds. FIG. 7 demonstrates that capsaicin and cinnamaldehyde increase nose temperatures for the fifteen minutes following ingestion, suggesting stimulation of the same autonomic thermoregulation pathway.

The chin temperature of the subjects was measured over the eighty minutes following ingestion of the various compounds. FIG. 8 shows a graph and a table of the chin temperature, relative to baseline, as a function of time elapsed after ingestion of the various compounds. FIG. 8 demonstrates that cinnamaldehyde increases chin temperature for a prolonged time after ingestion, indicating increased blood flow, probably reflecting sympathetic autonomic activity.

These results indicate that capsaicin and cinnamaldehyde might induce the same short term autonomic thermoregulation response by inducing a vasodilator reflex on the capillary of the nose. The increased sympathetic activity identified by measuring the facial temperature (increased blood flow on the chin) might explain the increased energy expenditure measured by indirect calorimetry.

Example 2

Human subjects were administered a composition comprising 4.8 ppm capsaicin or 350 ppm cinnamaldehyde. FIG. 9 shows a graph of the comparative taste testing results. 87.9% of the participants judged capsaicin intense to very intense, compared to only 20.5% for cinnamaldehyde. To achieve a similar effect on fat oxidation of capsaicin and cinnamaldehyde, the dose of capsaicin is about 1.5 times less than the maximum that can be used as a flavor (7 ppm according to Fenaroli's Handbook; Burdock, 2010), and the dose of cinnamaldehyde is about 17.5 times less than the maximum that can be used as a flavor (6191.0 ppm according to Fenaroli's Handbook; Burdock, 2010).

Example 3

The in vitro activity of hTRPA1 expressed in CHO cells was measured for 10 µM cinnamaldehyde and 0.3 µM zinc individually, as well as the combination. The results are shown in FIG. 10 and show a synergistic effect when cinnamaldehyde and zinc are combined (Cin+Zinc). C+ represents the experimental positive control for this test and is cinnamaldehyde at 50 mM which give a maximum efficacy according to a dose-response curve.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for improving a characteristic selected from the group consisting of insulin resistance, glucose tolerance, cognitive performance, cognition, mood, and memory, the method comprising administering to an individual in need thereof a composition comprising cinnamaldehyde and a compound comprising zinc, the compound is selected from the group consisting of zinc chloride, zinc sulfate, zinc lactate, zinc citrate, and mixtures thereof, and the composition is a food product in which the cinnamaldehyde:zinc ratio is 1:0.5 to 1:0.005 and the cinnamaldehyde is present at a flavoring concentration from 31.87 ppm to 100 ppm.

2. The method of claim 1 wherein the individual is selected from the group consisting of an infant born preterm, an infant experiencing intrauterine growth restriction, a pregnant woman suffering from gestational diabetes, a human suffering from insulin resistance, a human suffering from impaired glucose tolerance, and a human suffering from type II diabetes.

3. The method of claim 1 wherein the cinnamaldehyde is present in the composition in an amount that is safe and tolerable to ingest and, in combination with the zinc, effective to improve the characteristic selected from the group consisting of insulin resistance, glucose tolerance and a combination thereof.

4. The method of claim 1 wherein the composition comprises cinnamon essential oil extract that provides at least a portion of the cinnamaldehyde.

5. The method of claim 1 wherein at least a portion of the cinnamaldehyde is selected from the group consisting of isolated cinnamaldehyde and synthesized cinnamaldehyde.

6. The method of claim 1 wherein the composition is administered to the individual at least once a day for at least one week.

7. The method of claim 1 wherein the individual has a condition selected from the group consisting of cognitive decline, mild cognitive impairment, dementia, a mood disorder, memory loss, and combinations thereof.

8. The method of claim 1, wherein the cinnamaldehyde:zinc ratio is 1:0.03.

* * * * *